US00PP23644P2

(12) United States Plant Patent
Hanes

(10) Patent No.: US PP23,644 P2
(45) Date of Patent: May 28, 2013

(54) ***PETUNIA* PLANT NAMED 'PEHY0003'**

(50) Latin Name: *Petunia hybrida*
Varietal Denomination: PEHY0003

(75) Inventor: Mitchell E. Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 89 days.

(21) Appl. No.: 13/317,533

(22) Filed: Oct. 20, 2011

(51) Int. Cl.
*A01H 5/00* (2006.01)

(52) U.S. Cl.
USPC ..... Plt./356.1

(58) Field of Classification Search ..... Plt./356.1
See application file for complete search history.

*Primary Examiner* — Annette Para
(74) *Attorney, Agent, or Firm* — Joshua L. Price

(57) ABSTRACT

A new *Petunia* plant named 'PEHY0003' particularly distinguished by the fairly large size, brilliant red-purple colored flowers with a weak pattern of dark veining, medium green foliage, good branching, early flowering, and is more floriferous throughout the season.

1 Drawing Sheet

Latin name of the genus and species of the plant claimed: *Petunia hybrida.*

Varietal denomination: 'PEHY0003'.

BACKGROUND OF THE NEW PLANT

The present invention comprises a new *Petunia*, botanically known as *Petunia hybrida*, and hereinafter referred to by the variety name 'PEHY0003'.

'PEHY0003' is a product of a planned breeding program. The new cultivar has fairly large size, brilliant red-purple colored flowers with a weak pattern of dark veining, medium green foliage, good branching, early flowering, and is more floriferous throughout the season.

'PEHY0003' originated from a hybridization made in August 2007 in a controlled breeding environment in Gilroy, Calif., USA. The female parent was the unpatented proprietary plant designated '1864-3' with amethyst flower color, smaller flower size, and a more upright plant habit.

The male parent of 'PEHY0003' was an unpatented proprietary plant identified as '1903-2' with purple-rose flowers, a less intense red-purple hue, and later flowering.

The resulting seeds were sown in December 2007. 'PEHY0003' was selected as one flowering plant within the progeny of the stated cross in March 2008 in a controlled environment in Gilroy, Calif.

The first act of asexual reproduction of 'PEHY0003' was accomplished when vegetative cuttings were propagated from the initial selection in March 2008 in a controlled environment in Gilroy, Calif.

BRIEF SUMMARY OF INVENTION

Horticultural examination of plants grown from cuttings of the plant initiated in March 2009, and continuing thereafter, has demonstrated that the combination of characteristics as herein disclosed for 'PEHY0003' are firmly fixed and are retained through successive generations of asexual reproduction.

'PEHY0003' has not been observed under all possible environmental conditions. The phenotype may vary significantly with variations in environment such as temperature, light intensity, and day length.

Plant Breeder's Rights for this cultivar were applied for in Canada on Dec. 17, 2010, #10-7132 and in the Community Plant Variety Office on Oct. 15, 2010, #2010/2184. 'PEHY0003' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

Figure 1:
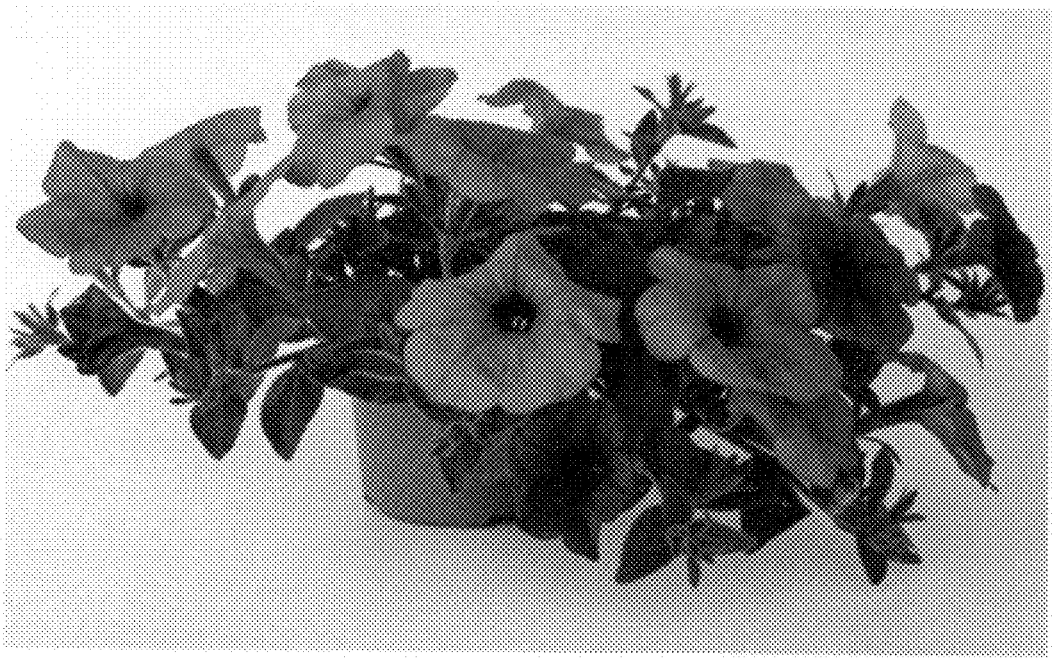
Figure 2:
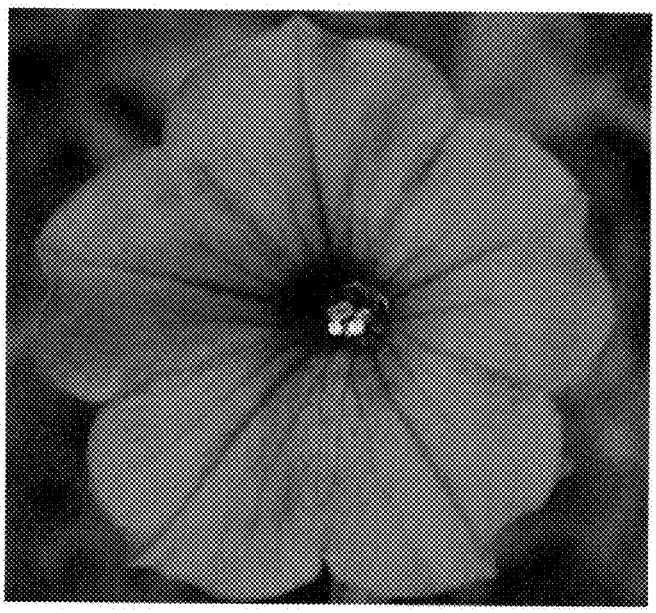

The accompanying photographic drawing shows typical flower and foliage characteristics of 'PEHY0003' with colors being as true as possible with an illustration of this type. The photographic drawing shows in FIG. 1. a flowering plant of the new variety and in FIG. 2. a close-up of the flowers.

DETAILED BOTANICAL DESCRIPTION

The aforementioned photographs were taken in April 2010 from plants growing in a greenhouse trial in Andijk, Netherlands. These plants were approximately 12-13 weeks of age.

The plant descriptions and measurements were taken in mid May 2011 in Andijk, Netherlands on 12 week old plants that were growing in 12 cm pots.

Color references are made to The Royal Horticultural Society Colour Chart (R.H.S.) 2001.

TABLE 1

DIFFERENCES BETWEEN THE NEW VARIETY 'PEHY0003' AND A SIMILAR VARIETY

| | PEHY0003' | 'Petpur' (U.S. Plant Pat. No. 17,261) |
|---|---|---|
| Flower color: | A more brilliant hue of RHS N66A to RHS N74A | Closest to RHS N74A |
| Flower vein color: | More purple hues | More greyed brown hues |

TABLE 1-continued

DIFFERENCES BETWEEN THE NEW VARIETY 'PEHY0003' AND A SIMILAR VARIETY

| | PEHY0003' | 'Petpur' (U.S. Plant Pat. No. 17,261) |
|---|---|---|
| Flowering response: | Earlier | Later |
| Reaction to cold conditions in spring: | Hardly affected, no damage | More susceptible |
| Petal apex shape: | Truncate to more cuspidate | Rounded |

Plant:

*Form, growth and habit*.—Initially mounding, then more spreading and decumbent, pinching enhances the number of branches.

*Plant height*.—11.0-15.0 cm.

*Plant height* (*inflorescence included*).—Mostly 12.0-16.0 cm.

*Plant diameter* (*width*).—45.0-52.0 cm.

Roots:

*Number of days to initiate and produce roots*.—18-24 days at about 22 degrees C.

*Type*.—Fine, fibrous, free branching.

*Color*.—RHS N1558D.

Foliage:

*Arrangement*.—Alternate, simple.

*Immature leaf, color upper surface*.—RHS 137C to RHS 137D.

*Immature leaf, color lower surface*.—Closest to RHS 144A.

*Mature leaf, color upper surface*.—RHS 137B to RHS 137C.

*Mature leaf, color lower surface*.—Between RHS 138A and RHS 144A.

*Length*.—4.4-5.2 cm.

*Width*.—2.6-3.3 cm.

*Shape*.—Elliptical to ovate, or even slightly rhomboid.

*Base shape*.—Obtuse or attenuate.

*Apex shape*.—Acute or obtuse.

*Margin*.—Entire.

*Texture, upper surface*.—Densely covered with short glandular hair.

*Lower surface*.—Densely covered with short hair, mainly along the leaf veins.

*Color of veins, upper surface*.—RHS 143C.

*Color of veins, lower surface*.—RHS 144A.

*Petiole color*.—RHS 144A.

*Length*.—0.2-0.3 cm.

*Diameter*.—0.3 cm.

*Petiole texture*.—Short glandular hair.

Stem:

*Quantity of main branches per plant*.—8.

*Color of stem*.—RHS 137B.

*Length of stem*.—35.0-40.0 cm.

*Diameter*.—0.2-0.3 cm.

*Length of internodes*.—2.5-5.5 cm.

*Texture*.—Dense, mostly glandular hairs of various lengths.

*Color of pedicel*.—RHS 143C, with a little RHS 177B anthocyanin just below the bud or inflorescence.

*Length of pedicel*.—2.4-4.0 cm.

*Diameter of pedicel*.—0.15-0.20 cm.

*Texture of pedicel*.—Densely covered with short glandular hairs.

Inflorescence:

*Type*.—Flowers solitary in upper leaf axis; flowers face mainly horizontally.

*Floret type*.—Funnel-shaped; 5 lobed petals; fused a the base.

*Blooming habit*.—Continuous flowering throughout the summer months, little affected by heat.

*Quantity of inflorescences per plant*.—Approximately 50-70.

*Lastingness of individual blooms on the plant*.—About 7-9 days.

*Fragrance*.—None.

Bud (just when opening):

*Color*.—Between RHS N77A and RHS N79A but a little greyer.

*Length*.—5.0-5.5 cm.

*Width*.—0.7-0.9 cm.

*Shape*.—Oblong.

Immature inflorescence:

*Flower horizontal diameter*.—5.0-5.5 cm.

*Color petals, upper surface*.—Closest to RHS 61A but more bluish.

*Color petals, lower surface*.—Between RHS 72A to RHS 72C.

Mature flower:

*Flower horizontal diameter*.—6.8-7.2 cm.

*Flower height* (*vertical*).—4.0-4.5 cm.

*Color upper surface*.—Between RHS N66A and RHS N74A but more 'brilliant', with RHS N79A veining, most distinct around the corolla opening and fading more towards the apex.

*Color lower surface*.—RHS 71B or RHS 72A.

All petals:

*Apex shape*.—Truncate to slightly cuspidate.

*Margin*.—Entire.

*Waviness of margin*.—Weak to medium.

*Petal lobation*.—Weak to medium.

*Petal texture, upper surface*.—Papillose, glabrous.

*Petal texture, lower surface*.—Papillose; very short glandular hair mostly at the margins and along the veins.

*Corolla tube color outside*.—RHS N77B.

*Corolla tube color inside*.—Mostly RHS N79A with some RHS N77A.

*Corolla tube length*.—3.0-3.3 cm.

*Corolla tube texture, outside*.—Pilose, glandular hairs.

*Corolla tube texture, inside*.—Glabrous.

Calyx:

*Color of sepal, upper surface*.—RHS 137A, slightly lighter basally.

*Color of sepal, lower surface*.—RHS 137D.

*Length*.—2.2-2.4 cm.

*Width*.—0.4 cm.

*Shape*.—Ensiform.

*Apex shape*.—Acute to obtuse.

*Base*.—Fused.

*Margins*.—Entire.

*Texture, upper surface*.—Densely covered with short glandular hairs.

*Lower surface*.—Covered with short glandular hairs, mainly along the edges.

Reproductive organs:

*Pistil*.—1.

*Length*.—1.8-2.0 cm.

*Style color*.—RHS 145A.

*Style length*.—1.6-1.7 cm.

*Stigma color*.—RHS 143B.

*Stamens*.—Quantity per flower 5. Color of filaments: RHS 157A. Length filaments: 1.0-1.5 cm. Anther color: RHS 97C. Anther length: 0.15 cm. Anther shape: Elliptical. Color of pollen: RHS 10D. Pollen amount: Moderate.

*Fertility/seed set*.—Has not been observed on this hybrid.

*Disease/pest resistance*.—Has not been observed on this hybrid.

What is claimed is:

1. A new and distinct variety of *Petunia* plant named 'PEHY0003' substantially as illustrated and described herein.

* * * * *

UNITED STATES PATENT AND TRADEMARK OFFICE

CERTIFICATE OF CORRECTION

PATENT NO. : PP23,644 P2
APPLICATION NO. : 13/317533
DATED : May 28, 2013
INVENTOR(S) : Hanes It is certified that error appears in the above-identified patent and that said Letters Patent is hereby corrected as shown below:

In the Specification

At column 3, line 26, delete "RHS N1558D" and insert therefor --RHS N155D--

At column 4, line 4, delete "fused a" and insert therefor --fused at--

Signed and Sealed this
Second Day of July, 2013

Teresa Stanek Rea
*Acting Director of the United States Patent and Trademark Office*